(12) United States Patent
Forbes et al.

(10) Patent No.: US 8,221,368 B2
(45) Date of Patent: Jul. 17, 2012

(54) APPARATUS FOR USE WITH OSTOMY DEVICES PROVIDING PROTECTION AND SOUND ATTENUATION OF A STOMAL APERTURE

(75) Inventors: Patricia Forbes, Oshawa (CA); Bill Forbes, Oshawa (CA)

(73) Assignees: Patricia Forbes, Oshawa, Ontario (CA); Bill Forbes, Oshawa, Ontario (CA)

( * ) Notice: Subject to any disclaimer, the term of this patent is extended or adjusted under 35 U.S.C. 154(b) by 190 days.

(21) Appl. No.: 12/801,973

(22) Filed: Jul. 6, 2010

(65) Prior Publication Data

US 2012/0010580 A1   Jan. 12, 2012

(51) Int. Cl.
*A61F 5/448* (2006.01)
*A61F 2/02* (2006.01)
(52) U.S. Cl. .......................................... 604/339; 600/32
(58) Field of Classification Search ........................ None
See application file for complete search history.

(56) References Cited

U.S. PATENT DOCUMENTS

| | | | |
|---|---|---|---|
| 4,203,445 A | 5/1980 | Jessup et al. | |
| 4,211,224 A | 7/1980 | Kubach et al. | |
| 4,372,308 A | 2/1983 | Steer et al. | |
| 4,721,508 A | 1/1988 | Burton | |
| 4,950,223 A | 8/1990 | Silvanov | |
| 5,178,614 A | 1/1993 | McDowell et al. | |
| 5,401,264 A | 3/1995 | Leise, Jr. | |
| 6,165,159 A | 12/2000 | Blanton | |
| 6,306,191 B1 | 10/2001 | McInerney et al. | |
| 6,485,476 B1 * | 11/2002 | von Dyck et al. | ............. 604/332 |
| 6,632,204 B2 * | 10/2003 | Guldfeldt et al. | ............. 604/349 |
| 6,689,111 B2 | 2/2004 | Mulhauser et al. | |
| 7,160,275 B2 | 1/2007 | Falconer | |
| 7,468,056 B2 | 12/2008 | Burt | |
| 2003/0236509 A1 | 12/2003 | Silvestrini | |
| 2007/0100308 A1 | 5/2007 | Miyairi | |
| 2007/0191794 A1 | 8/2007 | Cline et al. | |
| 2008/0015405 A1 | 1/2008 | Davies et al. | |
| 2008/0228155 A1 | 9/2008 | Longstaff | |
| 2010/0174253 A1 | 7/2010 | Cline | |
| 2011/0147114 A1 | 6/2011 | Bain et al. | |

FOREIGN PATENT DOCUMENTS

| | | |
|---|---|---|
| EP | 0319071 A2 | 6/1989 |
| GB | 2094153 | 9/1982 |
| WO | WO 2006/125933 A1 | 11/2006 |
| WO | WO 2011/079295 A2 | 6/2011 |
| WO | WO 2011/110140 A1 | 9/2011 |

OTHER PUBLICATIONS

Intellectual Property Office Search Report for Application No. GB1111100.2 dated Oct. 14, 2011.

* cited by examiner

*Primary Examiner* — Jacqueline Cheng
*Assistant Examiner* — Joshua Lee
(74) *Attorney, Agent, or Firm* — Mark D. Penner (57) ABSTRACT

The present invention is directed to an apparatus for use with an ostomate device. The apparatus of the present invention may provide protection and sound attenuation (e.g. reduction or elimination) of a stomal aperture for an ostomate having undergone an ostomy procedure. The present invention enables an ostomate safety when undergoing physical activity and confidence in social environments.

13 Claims, 7 Drawing Sheets

APPARATUS FOR USE WITH OSTOMY DEVICES PROVIDING PROTECTION AND SOUND ATTENUATION OF A STOMAL APERTURE

FIELD OF INVENTION

The present invention relates to an apparatus for an ostomy device, such as a sound attenuation device for use with ostomy devices which provides protection for ostomates.

BACKGROUND OF THE INVENTION

Ostomies are surgical procedures to create an artificial opening formed in the abdominal wall. A stoma in the abdominal wall is formed by a surgeon who brings a portion of the internal organ, such as the intestine, through the abdominal wall, thereby creating a temporary or permanent opening with the surface area called a stoma. Having undergone an ostomy, an individual must always keep an ostomy device, such as, for example, a colostomy bag, in position against the stoma to receive bodily waste discharged through the stoma.

A large number of ostomy devices for receiving bodily waste from individuals undergoing similar procedures ("ostomates") have been disclosed in the prior art, such as, for example, U.S. Pat. No. 5,693,035. These devices collect solid and liquid waste, along with flatus gasses, into a collection receptacle, bag or pouch as they are discharged from the surgically constructed stoma in the abdominal wall.

One goal of these devices is to increase the freedom of mobility of the ostomate and thus the wearer's ability to lead a normal life by participating in various activities. One disadvantage of such ostomy devices is the previously uncontrollable production of noise or sound that results from the exit of flatus gasses from the stoma, which can be embarrassing to the individual resulting in decreased comfort and social rehabilitation. The latter is particularly significant as it may negatively impact ostomates' confidence with regard to social interactions. The sound can be the result of vibrations of a portion of the mucous membrane of the stomal opening or aperture. The characteristics (i.e. volume. duration, etc.) of the sound may depend on a number of factors, including the velocity at which the flatus or intestinal gasses exits the stomal aperture, size of the aperture and also the positioning of the mucous membranes at the aperture of the stoma.

Ostomy devices that control release of waste material have been disclosed in the prior art, such as, for example, U.S. Pat. Nos. 6,221,041; 6,050,983; 4,406,657. Plugging systems have been proposed, which may provide a certain degree of lowering of the noise made by a stoma on and/or in which such a plugging system is inserted, such as, for example, U.S. Pat. No. 2,931,353. But these plugging devices can only be used instead of the aforesaid collecting bags.

Currently available ostomy products may not be designed to take into consideration the physical activities of the ostomate. For example, current products may not protect the stoma from external injury or pressure. Many ostomates have the physical health to allow them a full and active life. The stoma may be injured with relatively small force such as that provided during such physical activity, therefore providing a marked increased risk of injury to the stoma. Normal activities and in particular, physical activities such as sports, may therefore be dangerous for ostomates who use such devices, for example blunt force trauma injury.

There are shortcomings and drawbacks among the wide variety of ostomy products currently available. In light of the foregoing, there is a need, therefore, to provide for a sound attenuation device that also provides additional protection to the stoma.

SUMMARY OF THE INVENTION

A broad aspect of the present invention is an ostomy device that provides for sound attenuation of the sound made by the stoma upon release of flatus gases and/or the protection of the stoma from physical injury. The apparatus or device of the present invention comprises components that may be used separately or in combination. An aspect of the present invention is directed to a stomal insert while another aspect of the invention is directed to a stomal shield. In yet a further aspect of the present invention, both the stomal shield and the stomal insert may be configured to work together to affect sound attenuation and/or protection. It will be understood by a person skilled in the relevant art, however, that the above noted aspects of the present invention, namely the stomal insert and the stomal shield, may also be used separately to affect sound attenuation and/or protection.

An aspect of the present invention provides a shield to the stoma or any other area of concern. The stomal shield may be placed adjacent to the stoma as part of (e.g. integral with) or attached to the pouch of the appliance. The shield may provide internally or externally (e.g. an interior or exterior surface of the collection pouch of the ostomy appliance) and may cover a portion thereof or the entire pouch external side if desired. The shield is provided approximately opposed to the stoma. The stomal shield may be comprised of a cushion, a disc or a combination of the cushion and the disc. The cushion may be comprised of soft padding and may be of any size so as to be effective. The cushion may also be provided with one or more indentations or ridges so that when the cushion is placed on the stoma the indentation or ridges assist with directing the flatus gases in different directions for exit thereby modulating the release thereof (e.g. adjusting the direction and/or velocity of the gases) as well as affecting the mucous membrane positioning so as to impact the sound on exit of the gases. The cushion may be used in combination with the disc in order to affect sound attenuation when pressure is applied to the apparatus positioned adjacent to the stoma. The ostomate may apply pressure externally to the site when needed and the stomal shield may make contact with the stoma directly. This may affect the sound of the gas that is exiting from the stoma.

Another broad aspect of the invention is directed to a stomal insert having a protective support and a plurality of fingers extending from the protective support and adapted to be inserted into the stoma. In a preferred embodiment, the protective support of the stomal insert can be generally U shaped or O shaped. This support can provide some protection to the stoma from blunt trauma injury. Also provided on the fingers may be fringes that are designed to interact with the internal organ wall so to inhibit the movement thereof but not to penetrate or damage the mucosal lining of the organ wall. The configuration of the stomal insert may separate the mucus membrane of the stoma and modulate the vibrations of the membrane so as to impact the sound of flatus gases on exit of the stomal. When used in combination with the stomal shield, comprising the disc, cushion or disc/cushion combination, the stomal shield can interact with the support to spread the fingers of the stomal insert to affect the positioning of the mucous membranes. It will be further understood that the cushion or cushion/disc combination can affect the fingers of the stomal insert or can impact the positioning of the mucous membranes directly. In this way, an ostomate by applying pressure to the applicable area of the ostomy device will open the stomal aperture further so also to affect the sound of the gas leaving the stoma as well as providing protection to the stoma. The ostomate may apply pressure externally to the site when needed and the stomal shield may engage with the fingers of the insert. This may affect the sound of the gas that is exiting from the stoma.

An aspect of the invention is an apparatus for use with an ostomy device located proximally to a stoma, the apparatus comprising: (a) a stomal insert having a cap and a plurality of fingers extending from the cap, the stomal insert adapted to be inserted into the stoma; and (b) a shield having a semi spherical cushion portion attached to a disc portion, wherein the disc portion is attached to the ostomy device and the cushion portion can be biased against the cap.

Yet a further aspect of the invention is wherein the cap is generally U-shaped or generally circular.

Yet a further aspect of the invention is wherein each finger portion is adapted to conduct flatus gas towards the stoma Yet a further aspect of the invention is wherein each finger portion is generally tubular and may be hollow.

Yet a further aspect of the invention is wherein each finger portion extends through the cap so as to form a generally J-shaped vent portion.

Yet a further aspect of the invention is wherein each finger portion converges at a tip.

Yet a further aspect of the invention is wherein the fingers and the tip are comprised of a material that slowly erodes at the temperature within an internal organ (e.g. intestine).

Yet a further aspect of the invention is wherein the fingers and the tip are comprised of a solid material suitable for medical uses.

There is also provided the use of a slowly eroding material that melts at body temperature—to insert a device of the present invention into a stoma. The material may be used in the production of the stomal insert and for a tip adapted for use in the insertion of the stomal insert. The stomal insert and the tip can be absorbed or be expelled by the ostomate.

BRIEF DESCRIPTION OF THE DRAWINGS

The foregoing and other objects, features and advantages of the present invention should become apparent from the following description when taken in conjunction with the accompanying drawings.

DESCRIPTION OF THE PREFERRED EMBODIMENTS

The description that follows, and the embodiments described therein, is provided by way of illustration of an example, or examples, of particular embodiments of the principles and aspects of the present invention. These examples are provided for the purposes of explanation, and not of limitation, of those principles and of the invention.

In the following specification, the term "stoma", "stomal aperture" and "stomal opening" shall be understood to refer to any surgically constructed opening, which connects a portion of the body cavity to the outside environment. Typically, stomas are provided in the abdominal wall of an ostomate that has undergone some form of ostomy procedure where a stoma is created (so as to permit the passage of waste or discharge there through).

It will be understood by a person skilled in the relevant art that the term "ostomy procedure" refers to any surgical procedure that creates a stoma for the discharge of body waste. An ostomy procedure may be performed as a result of or due to a number of conditions, including, but not limited to, cancer, colitis, Crohn's disease, diverticulitis, imperforate anus, bladder cancer, Hirschsprung's disease or trauma. It will be understood that there are different types of ostomies performed depending on how much and what part of the intestines or other internal organs (e.g. bladder) is removed from a ostomate. For example, a colostomy can be performed when a portion of the colon (large intestine) is brought to the surface of the abdominal wall to allow stool to be eliminated. An ileostomy can be performed when an opening is created in the small intestine to bypass the colon for stool elimination. The end of the ileum, which is the lowest part of the small intestine, is brought through the abdominal wall to form a stoma and is called an ileostomy. An ileostomy might be performed due to ulcerative colitis, Crohn's disease, or familial polyposis. A urostomy is an opening for the urinary system. A urostomy is made in cases where long-term drainage of urine through the bladder and urethra may not be possible. It will be understood that the apparatus of the present invention could also be used for protection of the urostomy or for an area of fluid drainage such as a drain from a wound site.

It will be further understood by a person skilled in the relevant art that the term "ostomy device" or "ostomy bag" refers to an ostomy pouching system or apparatus that provides a means for the collection of waste from the biological system (such as; colon, ileum, jejunum) diverted as a result of the ostomy procedure. Ostomy devices or bags are also sometimes referred to as "appliances". Such ostomy devices or appliances are well known in the art and generally comprise a mounting plate, also referred to as a wafer or a flange, which is attached to the skin with an adhesive in an air- or water-tight seal, and a collection pouch that may be attached mechanically to the mounting flange. The flange is affixed to the skin and has an opening that is in communication with the stoma. The collection pouch of the ostomy device also has an opening that operates such that when the pouch is sealedly connected (e.g. connected so as to create an air- and water-tight seal between the pouch and the mounting plate) to the mounting plate, the material (e.g. solid, liquid and gas waste material) that is outputted or released from the stoma is collected in the collection pouch. In operation, therefore, the ostomy device allows the stoma to drain into the collection pouch, while protecting the surrounding skin from contamination. It will be understood that a number of different ostomy device designs are well known to those skilled in the relevant art, including, one- and two-piece designs, two-piece designs allow the changing and use of multiple pouches while retaining the wafer/baseplate for several days. The selection of systems varies greatly between individuals and is often based on personal preference and lifestyle. In operation, it will be understood to a person skilled in the relevant art that ostomy devices allow the ostomate to lead an active lifestyle that can include all forms of sports and recreation. The embodiments of the present invention are not, therefore, restricted to specific designs or configurations of ostomy devices. The embodiments of the present invention can be used with any ostomy device having a structure substantively similar to the structure noted above. It will be understood that the disc and cushion can be either inside or outside of the ostomy pouch adjacent to the stoma.

It will be understood by a person skilled in the relevant art that the term "ostomate" as used herein refers to individuals who have undergone an ostomy procedure and wear an ostomy device. The present invention is directed to providing ostomates (e.g. persons having undergone an ostomy procedure and wearing an ostomy device) with an improved psychological adjustment, privacy, security and ability to pursue a variety of physical activities through increased confidence, comfort and safety. The embodiments of the present invention may facilitate daily life for the ostomates and may allow ostomates to pursue active, fulfilling and productive lives without any significant limitations of activity.

An embodiment of the present invention provides a means of attenuation (e.g. reduction or elimination) of the sound made from the emission of waste material (e.g., flatus gases) through the stoma or stomal aperture thereby enabling user confidence in social environments. An aspect of the present invention is directed to achieving such sound attenuation by adjusting the size and/or shape of the stomal aperture. In one aspect of the invention, the adjustment of the size and/or shape of the stomal aperture may be achieved by pressure applied to the stomal aperture through an embodiment of the present invention when placed adjacent to the stoma inside or outside the ostomy bag. In another aspect of the invention, the adjustment is achieved by insertion of a device into the stomal aperture so as to decrease any noise associated with the release of waste material from the stomal aperture. In yet another aspect of the invention, the sound attenuation may be achieved by applying the two aspects in combination, namely adjusting the size and/or shape of the stomal aperture and inserting a device into the stomal aperture so as to decrease any noise associated with the release of waste material from the stomal aperture. These two aspects of the invention coordinate the exit of the flatus by the cushion spreading the fingers of the stomal insert device.

A further embodiment of the present invention also provides a means of protecting the stoma. An aspect of the present invention is directed to achieving such protection by the stomal device providing a movable barrier against the stomal aperture.

It will be understood that the embodiments of the present invention may be used to compliment an ostomate's existing ostomy devices and little or no change may be necessary for the use of the embodiments of the present invention. The embodiments of the present invention may be in addition to the standard ostomy devices currently in everyday use and could be added whenever an ostomate felt a need therefor, at the ostomate's discretion. The embodiments of the present invention would not affect the discharge of waste materials.

Figures 1, 2:
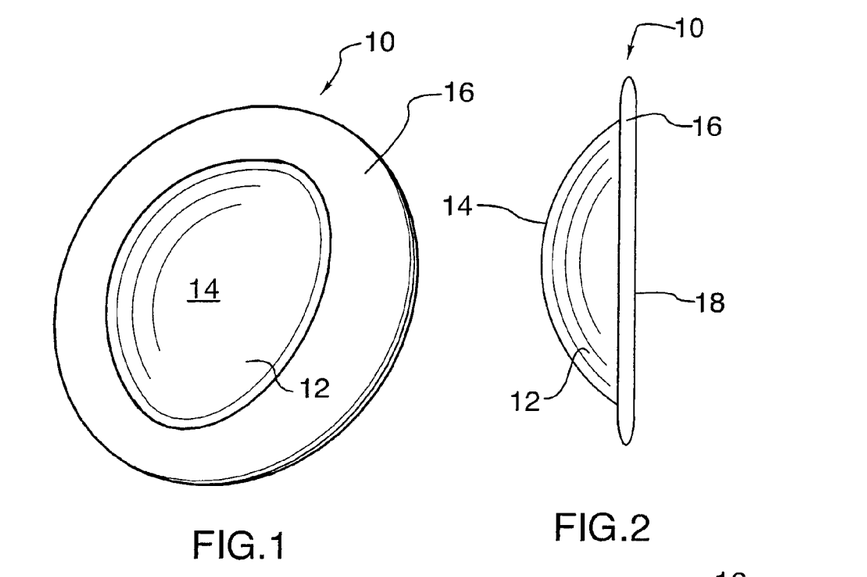
FIG. 1 is a perspective view of an embodiment of the present invention.
FIG. 2 is a side view of the embodiment provided in FIG.
Figure 11:
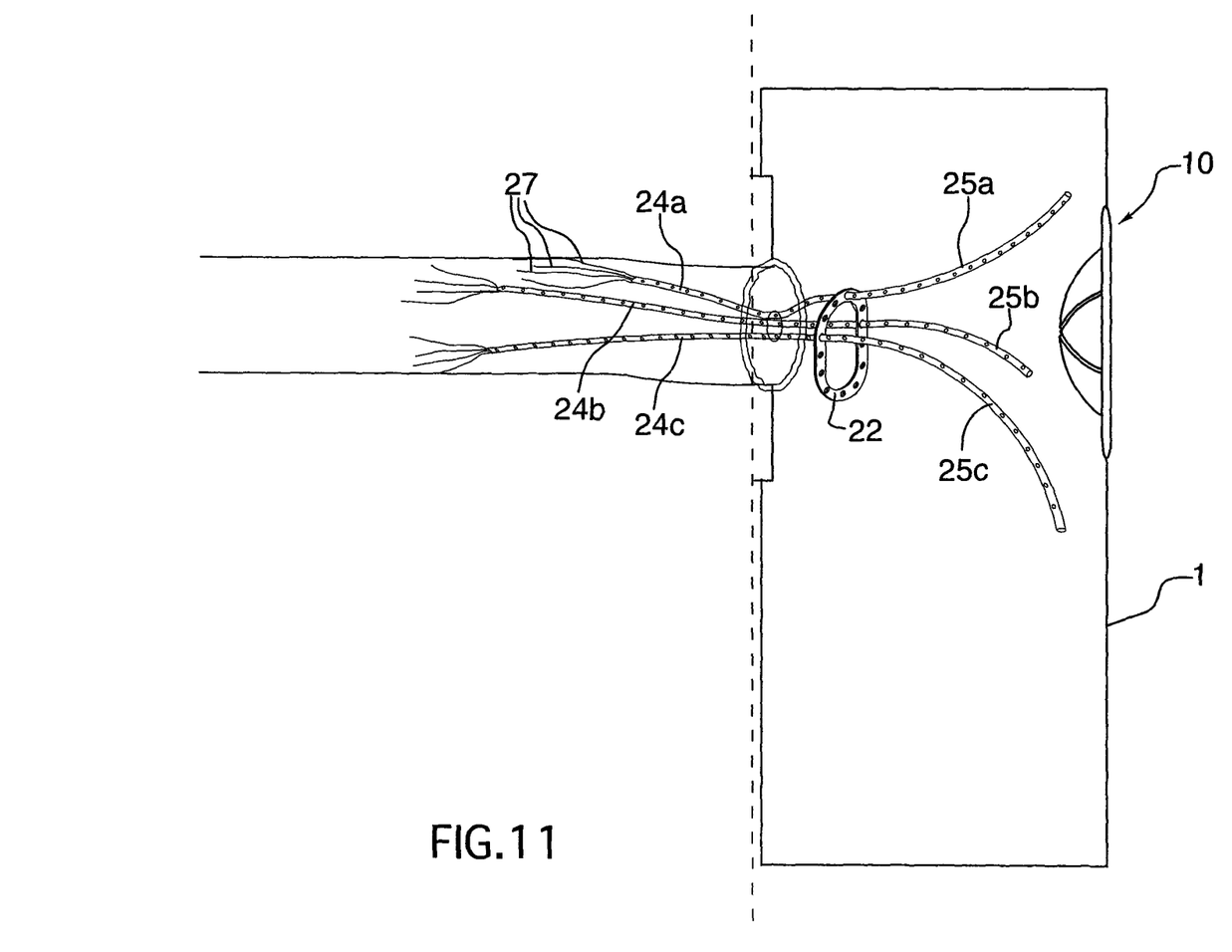
FIG. 11 is a perspective view of a further embodiment of the present invention.
Figure 12A:
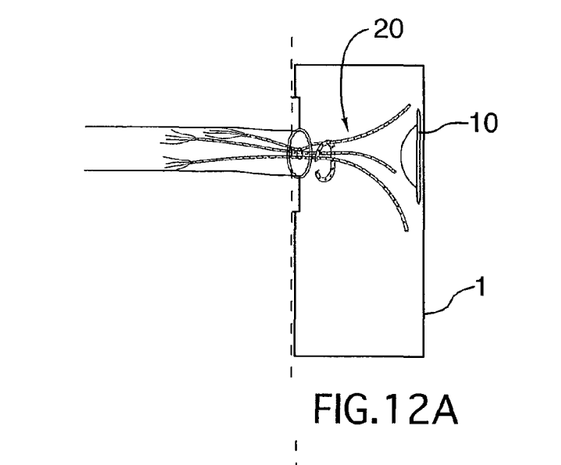
FIGS. 12A to D are views of further embodiments of the present invention.
Figure 12B:
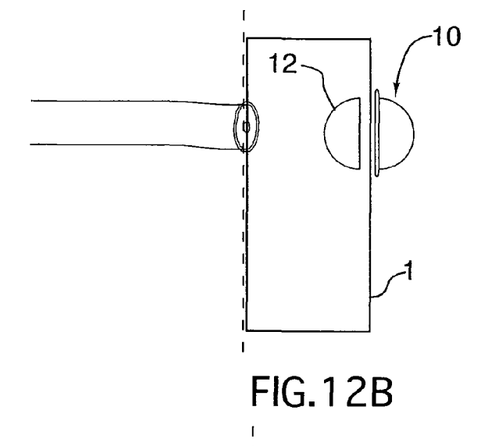
Figure 12C:
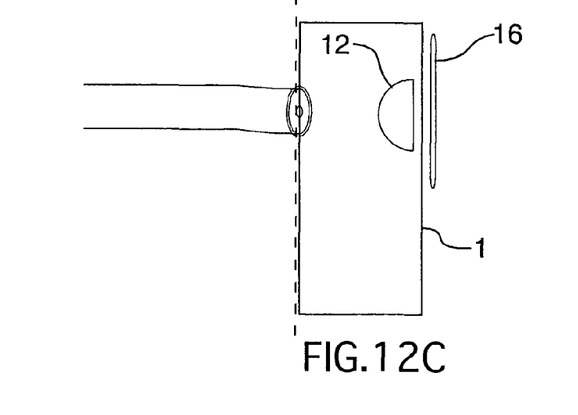
Figure 12D:
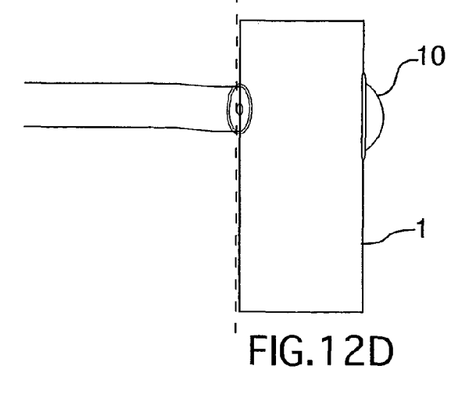

As shown in FIGS. 1 to 7, device 10 is provided that may be attached to the pouch portion 1 of an ostomy device (see FIGS. 11 and 12). It will be understood that device 10 can be mounted internally within collection pouch 1 (e.g. mounted to an interior surface of the collection pouch (see FIG. 12A)) or externally of collection pouch 1 (e.g. mounted to an exterior surface of the collection pouch (see FIG. 12B)). Device 10 can be used to adjust the surface tension of the stoma as well as change the direction and/or speed or rate of exit of waste material, including but not limited to flatus or intestinal gases. Device 10 can also be used to protect the stoma from mechanical abrasion or impact. As seen in FIGS. 1 and 2, there is provided disk 16 which may also be provided with a cushion 12. It will be understood that embodiments of the present invention include cushion 12 (see FIG. 4C and FIG. 12B and 12C), disk 16 (see FIGS. 3A and 3B as well as FIG. 12C) and more preferably, device 10 having both cushion 12 and disk 16 (see FIGS. 1 and 2 as well as FIGS. 12A, 12B and 12D). The cushion 12 could be of any size and also be used as a bumper or protective barrier.

Disk 16 has a first side 18 which can have an adhesive so that the device 10 can be attached to a surface (e.g. interior or exterior surface of collection pouch 1). It will be understood that any medically acceptable adhesive could be used in the present invention. In another embodiment, side 18 could be affixed to the collection pouch portion of the ostomy bag by means of tape or other adhesive product. It will be further understood that the device 10 may be affixed to the ostomy device roughly opposed to the location of the stomal opening such that when pressure is applied to a portion of the ostomy device, typically the collection pouch, the device 10 may be moved to come into contact with the stoma. As noted previously, it will be understood that the cushion/disc can be attached to either the inside or the outside of the pouch. The cushion/disc device may be manufactured either separately or as part of an ostomy device. When applied to the outside of the pouch (see FIG. 12), it may still function with the stomal insert device 20 but act as a protective barrier.

It will be understood that the protection portion of the present invention can be manufactured as part of the ostomy device pouch or manufactured as a standalone attachment. Device 10 can be used alone or in conjunction with other devices such as device 20, described below.

Figure 4A:
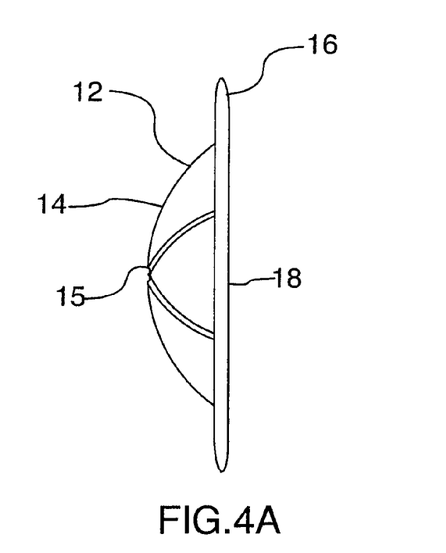
FIGS. 4A, B and C are views of an embodiment of the present invention.
Figure 4B:
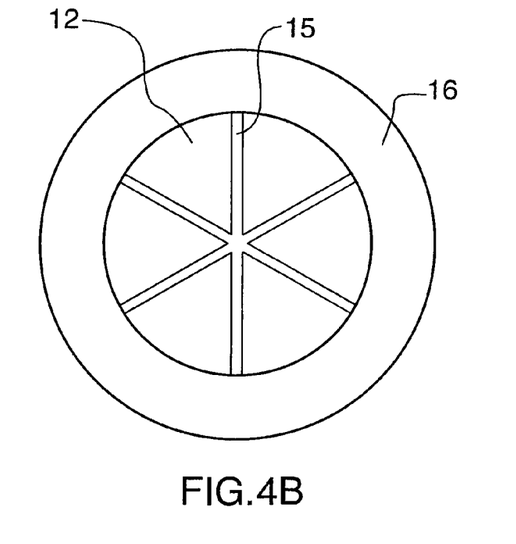

The cushion 12, in a preferred embodiment, comprises a generally half moon or half spherical shaped portion with a curved surface and a generally flat surface 14 that may be attached to disk 16. Cushion 12 can be made of a solid, soft, flexible material suitable for medical applications or alternatively could be saline or air-filled but having the general half moon shape. In a preferred embodiment, cushion 12 may be provided a pattern 15 of lines that dissect the cushion into quarters, eighths, sixteenths, etc. Portion 12 may also have indentations, grooves or patterns 15 (see FIGS. 4A and 4B) on the curved surface thereof to assist in conducting the release of the gas in different directions. The pattern 15 of cushion indentations are provided so that when cushion 12 may be positioned adjacent the stoma the indentation directs the flatus gases in different directions for exit and thereby adjusts the velocity of the gases and affects the mucous membrane positioning and therefore the sound on exit of the gases. The generally flat surface 14 of the cushion 12 may be attached to disk 16 with a medically acceptable adhesive product well known in the art. The disk 16 can be made from cardboard, plastic, rubber, metal or another suitable material.

Figures 5, 6, 7:
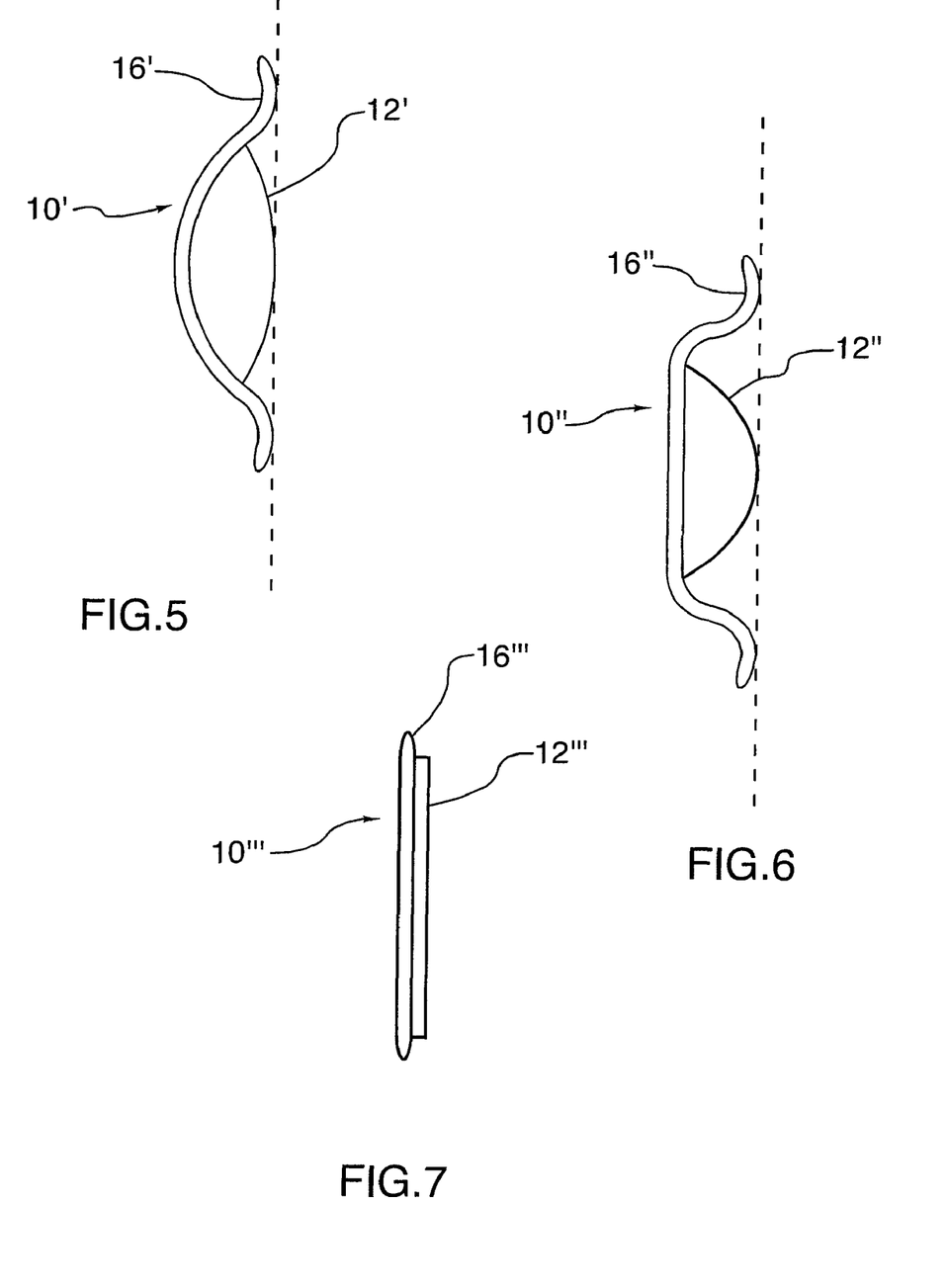
FIG. 5 is a side view of a further embodiment of the present invention.
FIG. 6 is a side view of a further embodiment of the present invention.
FIG. 7 is a side view of a further embodiment of the present invention.

As shown in FIGS. 1 to 3 and FIGS. 5 to 7, it will be understood that any configuration that provides protection to the stoma may be used in the present invention. In one embodiment, the device 10 may consist of disk 16 alone (see FIGS. 3A and 3B as well as FIGS. 12A to 12D). Alternatively, other embodiments may be provided as shown in FIGS. 5 and 7. As shown in FIG. 5, there is provided device 10' which may be provided with cushion 12' and disk 16. In another embodiment, as shown in FIG. 6, there is provided device 10" wherein disk 16" may be generally U-shaped. As shown in FIG. 7, disk 16'" and cushion 12'" may be generally flat. It will be understood that any combination of these various embodiments may be employed.

In operation, device 10 having cushion 12 assists with adjusting the surface tension of portions of the mucous membrane of the stomal aperture to change the manner in which such membrane portions rest. During use, cushion 12 of device 10 may be brought into contact or rest in contact with the stomal opening such that the surface tension which holds portions of the mucous membrane together may be reduced. With cushion 12 adjacent to or in contact with the mucous membranes, device 10 may decrease the degree to which mucous membrane portions are in contact with one another and assist the membrane portions to open. When material exits the stomal opening, any vibration of the membrane is therefore reduced or eliminated which in turn reduces the noise associated with the passage of material. An ostomate can manually apply pressure externally to the pouch at the location of the device when material is expelled which, in turn, may apply pressure to disc 16 of device 10 thus decreasing membrane contact even further thus reducing or eliminating the production of any sound. The device 10 could be an add-on to any existing pouch with the use of glue like or tape application on the side of the ostomy bag opposite the stomal aperture. The device 10 could also be built into any existing ostomy pouch product on manufacture.

Figure 3A:
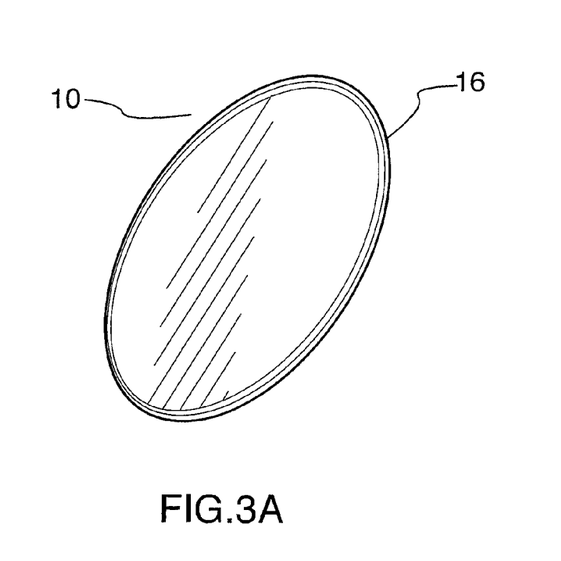
FIG. 3A is a perspective view of a further embodiment of the present invention.
Figure 3B:
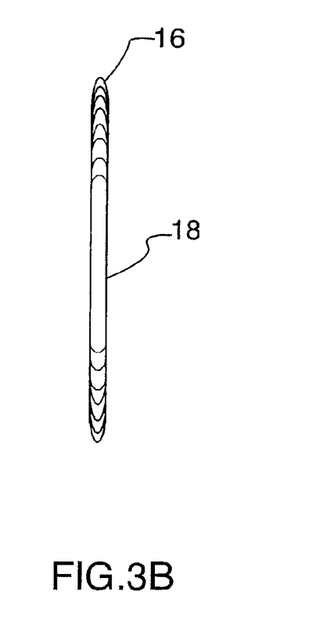
FIG. 3B is a side view of the embodiment provided in FIG. 3A.
Figure 4C:
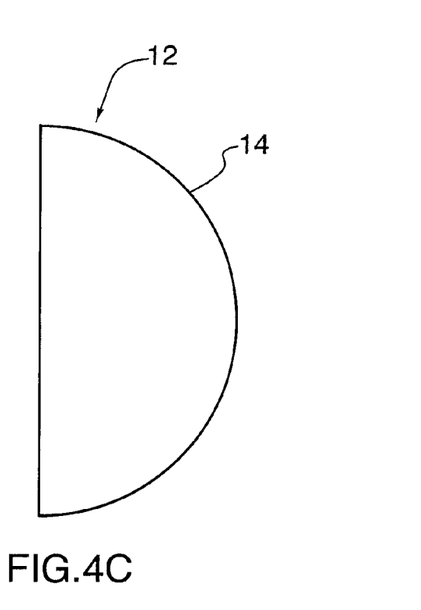

In another embodiment, the device also provides protection due to the cushioning effect from blunt trauma injury. It provides the stoma (which protrudes from the abdomen) with a soft pad for protection thus reducing the possibility of injury to the ostomate or wearer of the ostomy device. It will be understood that any configuration that provides protection to the stoma may be used in the present invention. For example, the embodiment shown in FIG. 3A provides device 10 wherein only disk 16 is provided for protection. Yet another embodiment, as shown in FIG. 4C, provides that cushion 12 may be used alone. Alternatively, another embodiment shown in FIG. 1 provides device 10 which may provide a generally half moon shaped portion 12 on disk 16. With both embodiments, it is possible to protect the stoma from injury, due to trauma.

In a preferred embodiment of the present invention, the diameter of the disc 16 can be sized to be of or greater than the diameter of the stoma. The cushion 12 could have varying shapes from generally flat (see FIG. 7) to a ½ moon shape (see FIG. 2, for example) and, in a preferred embodiment, may be comprised of soft medical material to protect the fragile mucous membrane. Disc 16 or cushion 12 could be made from any soft material that is medically suitable and well know in the art. Alternatively, disc 16 could be made from non flexible material, particularly when used in conjunction with cushion 12. As the stoma is a fragile mucous membrane, a firm shield like disc could be a benefit to reduce the degree of injury if the stoma were to be struck. Alternatively the disc with cushion could be chosen and again may be placed adjacent to the stoma and may add an additional layer of protection. The embodiment of the present invention may be chosen by the ostomate wearing the ostomy device with the understanding of its limitations for protection and with the persons assessing for themselves, its benefits and to be always mindful to limit any bulging under the clothing (if this is done incorrectly it could discourage the ostomate from using the product). Each individual could then choose from many different sizes of discs and different widths and heights of cushions most suited to their needs and thereby allowing individual choice not based on the size of the stoma alone. Variations of sizes of all items could be available. The disc and cushion could be manufactured alone or together and could be manufactured as part of the pouch or sold individually as an aftermarket product (see FIGS. 12A to 12D).

As noted in U.S. Pat. No. 6,165,159, there is a persistent and serious problem with conventional ostomy devices in that intestinal gas passes into and accumulates in the bag along with the fecal material. This pressurizes the bag, so that an unsightly bulge develops under the persons clothes. Moreover, unless the pressure is quickly relieved, the pressure can cause the adhesive wafer on the mounting plate to detach from the skin around the stoma. To avoid these consequences, the person must excuse themselves immediately upon detecting the gas build up and proceed to a restroom in order to empty the bag. At minimum this is a nuisance and under certain circumstances can be extremely embarrassing. It is believed that there is a current and future need for the use of larger elongated pouches, such as for example, Hollister number 3873. It will be understood that a larger pouch may be beneficial for comfort as this may allow for a lower profile of the pouch as gas accumulates. The larger pouch may allow for less bulging and increase the time between releases and therefore allow for better use of the stomal sound adjuster. By using the larger bag sizes in combination with the devices of the present invention, there may be a significant improvement in lifestyle comfort in reference to ostomy management. The protective aspect of the disc and the disc with cushion may be a matter of personal choice but may always remain an important asset regardless of the sizes needed.

The device 10 may assist with adjusting the surface tension of portions of the mucous membrane of the stomal aperture to change the way in which such membrane portions rest. During use, half moon portion or ½ sphere cushion shape 12 of device 10 may be in contact with the stoma and stoma opening such that the surface tension which holds portions of the mucous membrane together may be adjusted. With the portion 12 in contact with the mucous membranes, device 10 may decrease the degree to which mucous membrane portions are kept closed, and allow the membrane portions to open more easily. When material exits the stomal opening, the vibration of the membrane is therefore reduced or eliminated. A person can manually apply pressure externally to the pouch at the location of the device when gas is expelled which, in turn, may apply pressure to disc 16 of device 10 thus changing the direction of and decreasing the velocity of exiting flatus gases further reducing or eliminating the production of any sound.

Another aspect of the present invention is directed to achieving such sound attenuation by adjusting the size and/or shape of the stomal aperture. In such an embodiment, the adjustment is achieved by insertion of a device into the stomal aperture so as to maintain the stomal aperture open. A preferred embodiment comprises a device that enters a stoma where an ostomate may insert the device into the stoma so as to open the stoma thus allowing waste material to escape. Such an embodiment, by affecting the aperture of the stoma (e.g. changing the shape and size of the opening) separates the membranes to cause less vibration and therefore reducing the perceptible noise or sound when the flatus gas escapes from the stoma. It will be understood that the cushion device and fingers of the stomal insert device complement each other.

Figure 8A:
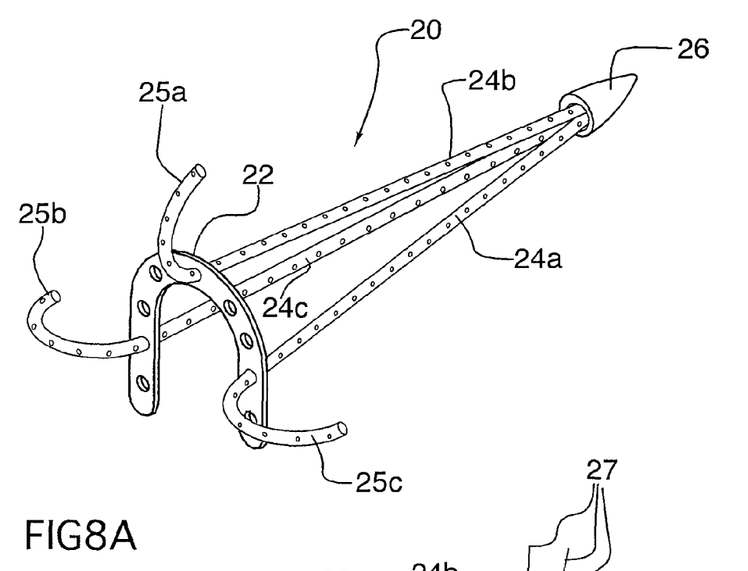
FIGS. 8A and B are perspective views of a further embodiment of the present invention.
Figure 8B:
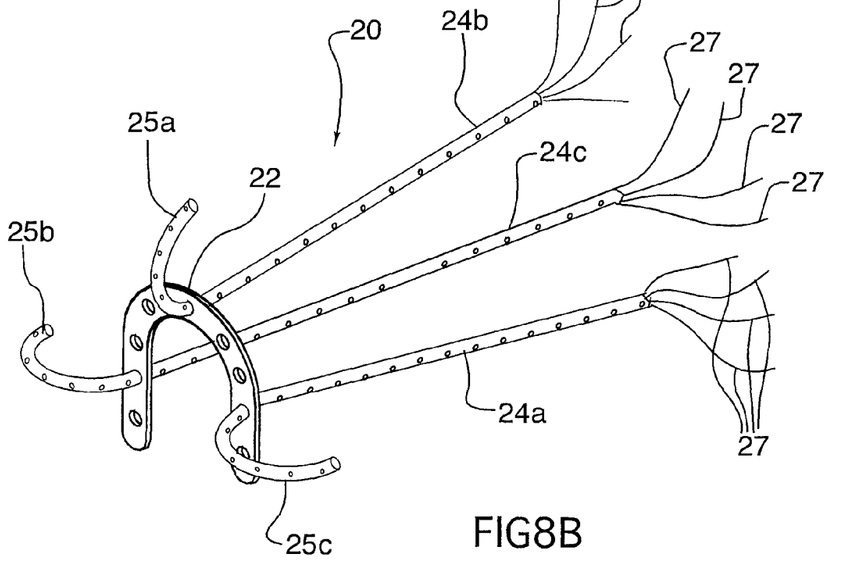
Figure 9:
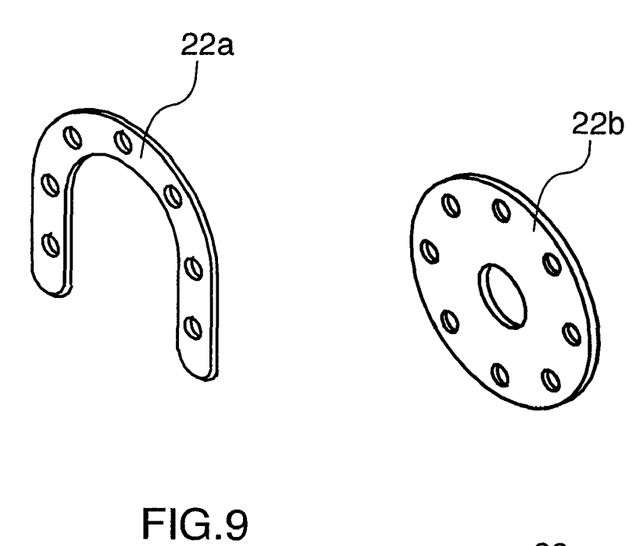
FIG. 9 is a perspective view of embodiments of the present invention.

This further embodiment is described in greater detail below. As shown in FIG. 8, there is provided stomal insert device 20. Stomal insert device 20 functions to separate the mucous membranes of the stoma allowing the gas to exit without causing the soft tissue of the stomal aperture to vibrate. The stomal insert device 20 has a generally C shaped support or cap structure 22 and extending therefrom are a plurality of hollow tube like flexible fingers, 24a, 24b and 24c. In a preferred embodiment, as shown in FIG. 9, the support portion may be generally U-shaped (22a). It will be understood that the support portion could also be generally O-shaped (22b). While only three figures are provided, it will be understood that any number of finger portions could be used. It will be understood that fingers 24a, 24b and 24c are sufficiently flexible to allow insertion into and movement within the stoma.

Vent portions 25a, 25b and 25c of the respective hollow tube like fingers 24a to 24c extend from support or cap 22 away from the tip 26. One function of vent portions 25a to 25c is to stop the passage of the entire device 20 into the stomal lumen. Tube like finger portions 24a to 24c can be flexible and hollow with a plurality of the vents extending along the length of the finger from 22 to tip 26. The vents allow for the release of intestinal gases through the applicable vent portions. The stomal insert device 20 could be made from soft rubber like material, suitable for medical use and presently in use for internal use or could be of a natural gelatine material that may slowly erode, breakdown or melt at the temperature within the internal organ (e.g. intestine) after a period of a few hours. A new stomal insert device could then be re-inserted as needed.

The finger portions may also have fringes 27 as shown in FIG. 8B, which are designed to engage with the intestinal wall so as not to penetrate or damage the mucosal lining.

In a preferred embodiment, the stomal insert device 20 may have a tip 26 which may be comprised with material that could slowly erode, breakdown or melt at the temperature within the internal organ (e.g. intestine) after a period of a few hours after being introduced into the stoma. Tip 26 can be bullet shaped to assist with insertion. Tip 26 could comprise of a water soluble gelatine like product, a solid food product (such as, for example, a grain based product that could dissolve over time) or inert viscoelastic polymers (such as, for example, hydroxypropyl methylcellulose such (Hypromellose)). An insertion device 29 (see FIG. 10) can engage with tip 26 so as to allow for insertion of the stomal insert device into the lumen of the stoma. It will be understood that any such material may then be absorbed or expelled by the ostomate. Once tip 26 is so absorbed or expelled, the fringes may be free to engage with the intestinal wall.

As seen in FIG. 8, the finger portions 24a, 24b and 24c may converge towards a point corresponding to tip 26 or remain biased outwardly so as to hold the stomal aperture open thus separating the mucous membrane of the stoma allowing gas to escape in an unobstructed manner. This may reduce the vibration that occurs when portions of the mucous membrane are in contact, resulting in sound attenuation. In a preferred embodiment, stomal insert device 20 may have a smaller width at an end distal to the cap or support 22, which rests in the stomal lumen, and the fingers may be biased outwards proximal to the cap/support 22, which remains at the stomal aperture, so as to have a greater width at the proximal or cap/support end than the distal or tip end. The resulting width of the support 22 and the distal end of the fingers shall be sufficiently large so as to maintain the stomal aperture open and the portions of the mucous membrane thereof not in contact with each other. It will be understood that the actual size of the devices can be adjusted depending on the application, but the width at the proximal end can be the width of a pencil while the width at the distal end can be approximately 3 to 6 inches. It will be further understood, however, that the external size of the stoma and the internal lumen may vary such the size of the devices of the present invention may vary accordingly.

The fingers and support of stomal insert device 20 may be made of soft rubber so as to reduce the risk of intestinal wall irritation upon insertion. The support portion 22 can be C-shaped or O-shaped (see FIG. 9) so as not to occlude the aperture and may be placed at the opening of the stoma to allow for the exit of waste. The C-shape support 22 prevents the stomal insert from entering the stoma. The rubber material may be chosen to have the characteristics to stay in contact with the walls of the internal organ (e.g. intestine) for support. In a preferred embodiment, the diameter or width of the support portion can approximately 2 inches to approximately 6 inches. It will be understood, however, that the width or diameter of the support portion may vary depending on the nature of the application.

Vent portions 25a to 25c located on the distal end of stomal insert device 20 may conform to the shape of the pressure device 10 (i.e., conform to cushion 12), so that the two devices may work together. The cushion/disc is designed to be used by the ostomate to flair the fingers of the stomal insert device as to open the aperture of the stoma and reduce vibration and thereby reduce sound. It will be understood that the pressure and stomal insert devices could be used together or could be used independently of one another.

Figure 10:
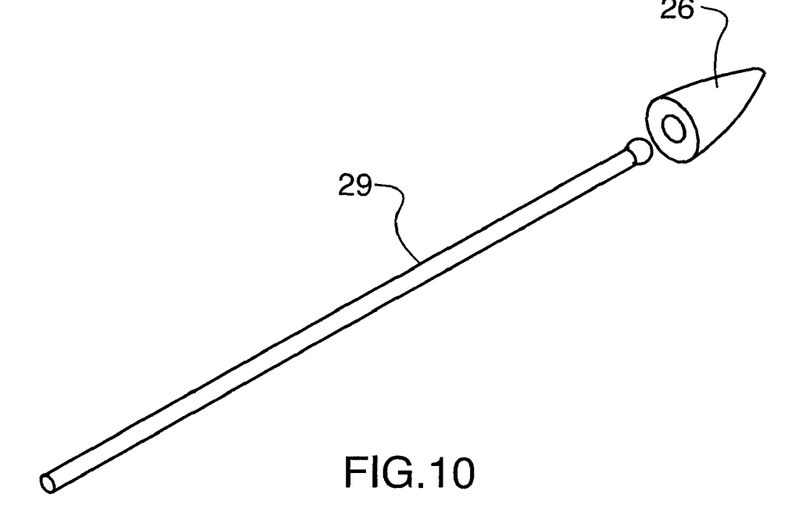
FIG. 10 is a perspective view of a further embodiment of the present invention.

The stomal insert requires an insertion means 27 that could be discarded after use and may be used by the ostomate to gently insert the stomal insert device into the stoma when required. As shown in FIG. 10, the insertion means, in a preferred embodiment, may comprise a soft rubber stick with an end shaped to engage tip 26. In a further embodiment, the stick portion may be approximately 8 inches long. FIG. 10 shows a handle having a ball tip. The ball may fit into the indentation on tip 26. It will be understood that any set of devices have a female/male type coupling could be used (not shown). After the stomal insert is inserted into the stoma, the insertion means can be removed.

In addition, the fingers which are above and below the support may function to separate the mucous membrane of the stoma. The external fingers 24a 24b 24c may engage with the pressure cushion or disc to assist with changing the aperture of the stoma and thereby reduce the sound and vibrations that occur with air exiting the stoma. The stomal insert enters the stoma with the insertion means that may engage with the stomal insert tip 26. With the stomal insert in place the disc/disc with cushion could be pressed against the vents of the stomal insert when needed and allow air to escape more freely from the opening. In this way the aperture and therefore the sound is adjusted in a manual method in addition to the effects of the dilatation of the stomal insert. The fingers of the stomal insert could be one or more but most commonly 3 or more and could be vented or not vented singular or joined. The stomal insert may have a large exterior support—C or O shape for example to prevent the stomal insert from entering the stoma. Variations of size may be needed as aperture and stoma sizes vary.

As shown in FIG. 8, Fingers portions 24a, 24b and 24c may not have any sharp edges and could be vented or unvented. 24a to 24c extend from disc or cap 22 away from the tip 26. Finger portions 24a to 24c can be hollow with a plurality of the vents extending along the length of the finger from cap 22 to tip 26. The vents allow for the release of intestinal gases through the applicable vent portions. In another embodiment, device 10 having cushion 12 assists with the operation of the stomal inserts. Device 10 and stomal insert 20 may operate co-operatively to adjust the surface tension of portions of the mucous membrane of the stomal aperture so as to change the manner in which such membrane portions rest. It will be understood that where the devices are used co-operatively, the size of disk 16 and support 22 may be substantially similar. During use, cushion 12 of device 10 may be brought into contact or rest in contact with the finger portions 24a to 24c such that the surface tension which holds portions of the mucous membrane together may be reduced and the fingers may be splayed so as to urge the stoma to open or remain open. With cushion 12 in contact with the stomal insert, devices 10 and 20 may decrease the degree to which mucous membrane portions are in contact, and allow the membrane portions to open easier. When material exits the stomal opening, any vibration of the membrane is therefore reduced or eliminated which in turn reduces the noise associated with the passage of material. An ostomate can manually apply pressure to the pouch at the location of device 10 when material is expelled which, in turn, may apply pressure to disc 16 of device 10 on the stomal insert 20 such that the stoma is urged open thus reducing or eliminating the production of any sound. The device 10 could be an add-on to any existing pouch with the use of glue like or tape application on the ostomy device in proximity to the stomal aperture.

Both disc device 10 and stomal insert device 20 may be designed to fit together to affect sound attenuation and to also offer a degree of protection to a stoma or a particular area such as a wound drain or urostomy site. The disc device 10, alone or in combination with cushion 12 can spread the fingers of the stomal insert to affect the positioning of the mucous membranes and in this way the ostomate can add pressure to the area and open the stomal aperture further and in this way can affect and minimize the sound of the gas leaving the stoma.

It will be understood, however that each of device 10 and stomal insert device 20 may be manufactured and used separately, with each providing protection and also an ability to affect the sound of gases expelled through a stoma.

A stomal insert having a support and a plurality of fingers extending from the support is adapted to be inserted into the stoma. The configuration of the support with fingers may separate the mucus membrane of the stoma and change the vibrations of the membranes and may affect the sound of gases on exit.

While preferred aspects of the present invention have been described in detail, various modifications, alterations, and changes may be made without departing from the spirit and scope of the present invention as defined in the appended claims.

We claim:

1. An apparatus for use with an ostomy device located proximally to a stoma, the apparatus comprising:
    (a) a stomal insert having a cap and a plurality of fingers extending from the cap, the stomal insert configured to be inserted into the stoma; and
    (b) a shield having a semi-spherical cushion portion attached to a disc portion, wherein the disc portion is attached to the ostomy device and the cushion portion can be biased against the cap, wherein each of the fingers configured to conduct flatus gas towards the stoma, and each of the fingers is a hollow tube and has a plurality of vents extending along the length of the finger.

2. The apparatus of claim 1 wherein the ostomy device has a collection pouch and the shield is attached to the collection pouch approximately opposed to the stoma.

3. The apparatus of claim 2 wherein the shield is attached to an interior surface of the collection pouch.

4. The apparatus of claim 2 wherein the shield is attached to an exterior surface of the collection pouch.

5. The apparatus of claim 4 wherein the cap is U-shaped or circular.

6. The apparatus of claim 1 wherein each the fingers converge at a tip.

7. The apparatus of claim 6 wherein the fingers and the tip are comprised of a material selected from the group consisting of water soluble gelatine, a grain based product, and hydroxypropyl methylcellulose.

8. The apparatus of claim 7 wherein the fingers and the tip are comprised of a solid material suitable for medical uses.

9. The apparatus of claim 8 wherein the apparatus provides attenuation of a sound made from an emission of waste material through the stoma.

10. The apparatus of claim 9 wherein apparatus provides a protective barrier to the stoma.

11. The apparatus of claim 10 wherein apparatus provides sound attenuation.

12. The apparatus of claim 11 adapted to treat the stoma resulting from of an ostomy procedure performed as a result of cancer, colitis, Crohns disease, diverticulitis, imperforate anus, Hirschsprung's disease or trauma.

13. The apparatus of claim 12 wherein the ostomy procedure is a colostomy or an ileostomy.

* * * * *